United States Patent [19]

Bailey

[11] Plant 4,429

[45] Jun. 26, 1979

[54] ROSE PLANT

[75] Inventor: Dorothy J. S. Bailey, Bakersfield, Calif.

[73] Assignee: San Joaquin Rose Company, McFarland, Calif.

[21] Appl. No.: 903,220

[22] Filed: May 5, 1978

[51] Int. Cl.[2] ..... A01H 5/00

[52] U.S. Cl. ..... Plt./11

[58] Field of Search ..... Plt./11

*Primary Examiner*—Robert E. Bagwill
*Attorney, Agent, or Firm*—Vincent G. Gioia

[57] ABSTRACT

A novel rose variety of the hybrid tea class characterized by flowers of unique bicolor tonality substantially as shown and described.

1 Drawing Figure

1

The present invention relates to a new and distinct variety of rose plant of the hybrid tea class, which was originated by my crossing the rose variety known as "Garden Party" as seed parent with the rose variety known as "Peace" as pollen parent.

Among the novel characteristics possessed by this new variety which distinguish it from its parents and all other varieties of which I am aware are: (1) flowers of bicolor tonality which combine basic ivory petal coloring with red washing or shading which holds to same coloring upon aging until red coloring extends to entire upper surface of petals, (2) high centered flowers of substantial petalage borne singly with petals remaining at first loosely rolled outward and (3) abundant foliage on a vigorous spreading plant. Asexual reproduction by budding of the new variety as performed in Kern County, Calif., shows that the foregoing and other distinguishing characteristics come true to form and are established and transmitted through succeeding propagations.

A main distinguishing feature of the new and improved rose variety is its unusual, attractive coloring of the flowers which are produced in good size and in large quantities. In addition, the sepals which are long and extend the length of the bud provide a pleasant contrast to the many-colored blooms.

The accompanying drawing shows typical specimens of the flowers and vegetative growth of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "11D" is plate 11D of the Royal Horticultural Society Color Chart.

Parentage: Seedling.
*Seed parent.*—"Garden Party".
*Pollen parent.*—"Peace".
Class: Hybrid tea.

The following observations are made of specimens grown outdoors at Kern County, Calif., during the month of June.

2

1. FLOWER

Blooming habit: Continuous.

A. Bud:
- (1) *Size.*—Medium.
- (2) *Form.*—Globular and sometimes pointed.
- (3) *Color.*—When sepals first divide: egg shell white with orange red "washing". When petals begin to unfurl: 11D with red washing. When half-blown: inside of petals — light yellow to ivory with light brushed effect washing of 54D on surface of petals — color is deepest at outer edge of petals blending to light yellow and ivory at base.
- (4) *Sepals.*—Long, extending to end of bud.
- (5) *Peduncle.*—Length — 3½ inches. Strength — erect. Color — 138A.

B. Bloom:
- (1) *Size.*—Average size when fully expanded 4 to 4½ inches.
- (2) *Borne.*—Singly.
- (3) *Form.*—High centered, petals remaining at first loosely rolled outward.
- (4) *Petalage.*—Number of petals under normal conditions — about 38.
- (5) *Color.*—Center of flower — 11A. Inside of petals — as above. Base of petals — 11A. Reverse of petals — 11B blending to lighter 11C.
- (6) *Color change.*—General tonality from a distance — ivory with orchid pink washing and holds to same coloring for more than three days after which the orchid pink (54D) pigment appears to spread and envelop the total upper petal surface.

C. Petals:
- (1) *Texture.*—Thick.
- (2) *Appearance.*—Inside — velvety; outside — satiny.
- (3) *Form.*—Ovoid.
- (4) *Arrangement.*—Regularly arranged, shingle-like.
- (5) *Petaloids in center.*—Medium.
- (6) *Persistence.*—Drop off clean.
- (7) *Fragrance.*—Slight.
- (8) *Lasting quality.*—Very long lasting on the plant and as a cut flower.

2. REPRODUCTIVE ORGANS

A. Stamens, anthers: Medium size, many.

(1) *Arrangement.*—Regularly arranged around styles.
(2) *Color.*—85B.

B. Pollen: —Color — 17D.
C. Styles: —Bunches; uneven length.
D. Stigmas: —Color — 55B.
E. Hips: —None observed.

3. PLANT

A. Form: Upright and spreading.
B. Growth: Vigorous, branching.
*Height attained.*—3 to 4 ft. during normal growing season.
C. Foliage: Compound of 5 to 7 leaves.
(1) *Size.*—Medium.
(2) *Quantity.*—Abundant.
(3) *Color.*—New foliage: upper side — 137C; under side — 139B. Old foliage: upper side — 137B; under side — 139A.
(4) *Shape.*—Ovoid.
(5) *Texture.*—Upper side — medium, waxed. Under side — rough.
(6) *Edge.*—Serrated.
(7) *Serration.*—Very small.
(8) *Leaf stem.*—Color — 147A; under side — 147C.
(9) *Stipules.*—Medium length; slightly bearded.

D. Wood
(1) *New wood.*—Color — 147B. Bark — smooth.
(2) *Old wood.*—Color — 146A. Bark — smooth.
E. Thorns:
(1) *Thorns.*—Quantity: on main stalks from base — ordinary; on laterals from stalk — few. Form: flat. Length: small. Color when young — 178C. Position: irregular.
(2) *Prickles*—Quantity: on main stalks — few; on laterals — none.
F. Plant's disease resistance:
*Mildew.*—Good.
*Blackspot.*—Good.
*Rust.*—Good.
G. Winter hardiness: Hardy.

I claim:

1. A new and distinct variety of rose plant of the hybrid tea class, substantially as shown and described, characterized particularly by flowers of unique bicolor tonality combining ivory petal coloring with orchid pink washing and which color is maintained until petal ages at which time the orchid pink pigment extends throughout the upper petal surface, high center and by a vigorous, branching plant of spreading and upright habit of growth.

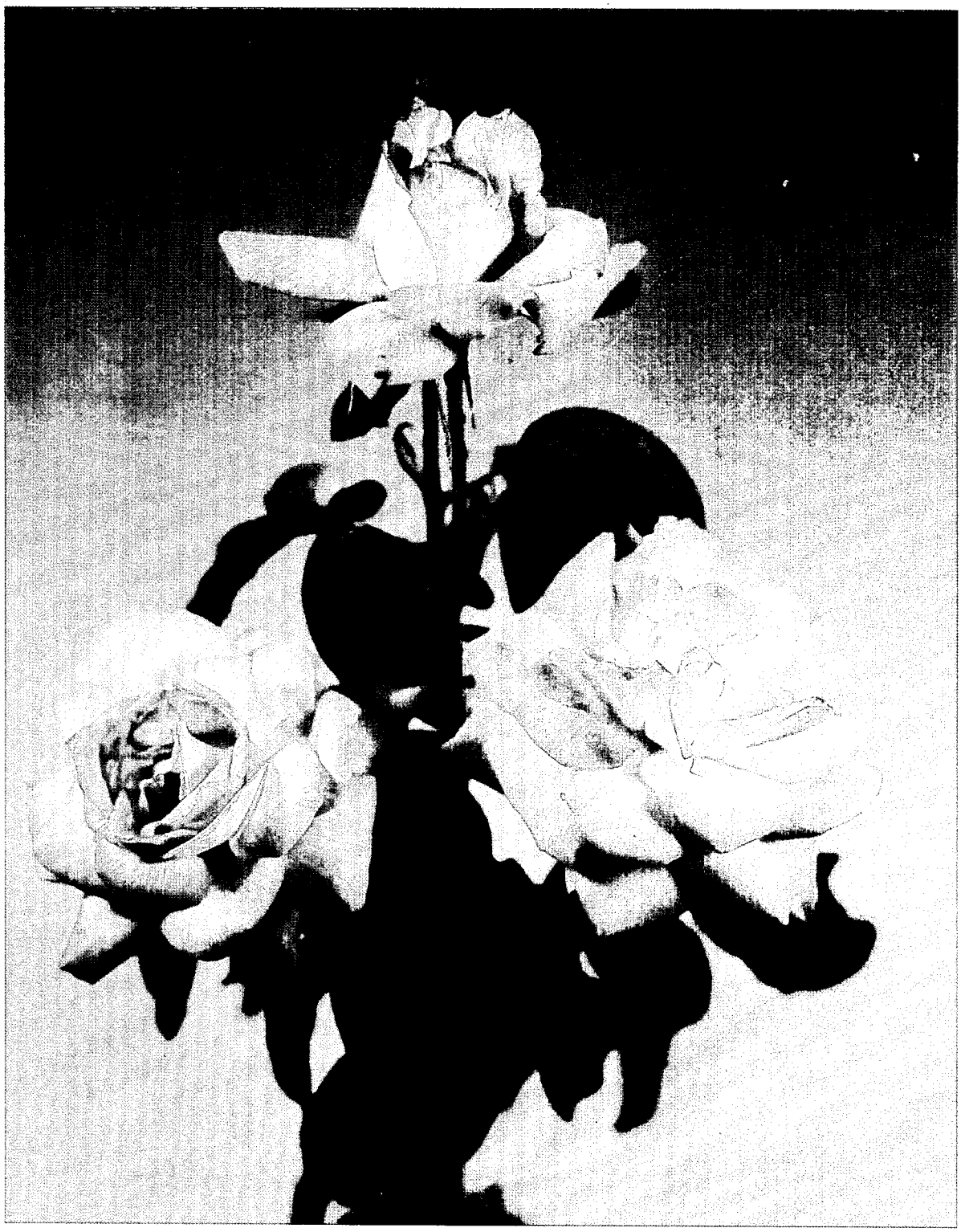

* * * * *